United States Patent
Balthasar et al.

(10) Patent No.: US 9,575,005 B2
(45) Date of Patent: Feb. 21, 2017

(54) INSPECTION APPARATUS

(71) Applicant: TOMRA SORTING NV, Leuven (BE)

(72) Inventors: Dirk Balthasar, Boppard (DE); Hartmut Harbeck, Wedel (DE)

(73) Assignee: TOMRA SORTING NV, Leuven (BE)

( * ) Notice: Subject to any disclaimer, the term of this patent is extended or adjusted under 35 U.S.C. 154(b) by 0 days.

(21) Appl. No.: 15/033,367

(22) PCT Filed: Nov. 3, 2014

(86) PCT No.: PCT/EP2014/073578
§ 371 (c)(1),
(2) Date: Apr. 29, 2016

(87) PCT Pub. No.: WO2015/063300
PCT Pub. Date: May 7, 2015

(65) Prior Publication Data
US 2016/0252461 A1 Sep. 1, 2016

(30) Foreign Application Priority Data
Nov. 4, 2013 (EP) ..................................... 13191395

(51) Int. Cl.
*G01N 21/00* (2006.01)
*G01N 21/85* (2006.01)
*B07C 5/342* (2006.01)

(52) U.S. Cl.
CPC .............. *G01N 21/85* (2013.01); *B07C 5/342* (2013.01); *G01N 2201/062* (2013.01);
(Continued)

(58) Field of Classification Search
CPC .............. G01N 21/9501; G01N 21/956; G01N 21/95607; G01N 21/8806; G01N 21/95; G01N 2021/95676; G01N 2201/061; G01N 21/8851; G01N 2021/8822; G01N 21/47; G01N 21/9503; G01N 21/00; G01N 21/4738
See application file for complete search history.

(56) References Cited

U.S. PATENT DOCUMENTS 5,462,176 A * 10/1995 Hereford ............... B07C 5/3425
131/905
6,060,677 A * 5/2000 Ulrichsen ............... B07C 5/342
209/577
(Continued)

FOREIGN PATENT DOCUMENTS

| CA | 2 697 636 A1 | 3/2009 |
|---|---|---|
| EP | 1 185 854 B1 | 11/2006 |
| WO | WO 2013/115650 A1 | 8/2013 |

OTHER PUBLICATIONS

International Search Report (PCT/ISA/210) issued on Jan. 14, 2015, by the European Patent Office as the International Searching Authority for International Application No. PCT/EP2014/073578.
(Continued)

*Primary Examiner* — Michael P Stafira
(74) *Attorney, Agent, or Firm* — Buchanan Ingersoll & Rooney P.C.

(57) ABSTRACT

An apparatus for inspecting a stream of matter including: a first and a second light source for emitting a first and a second light beam; a first and a second detector; a first scanning element adapted to redirect the detection area of the second detector from side to side across said stream, and a beam splitting element arranged to receive said first and second light beams, after they have been reflected against said matter, wherein said beam splitting element is adapted to guide said reflected first light beam towards said first detector and to guide said reflected second light beam towards said second detector.

22 Claims, 5 Drawing Sheets

(52) U.S. Cl.
CPC ............... *G01N 2201/068* (2013.01); *G01N 2201/0636* (2013.01); *G01N 2201/06113* (2013.01); *G01N 2201/06193* (2013.01)

(56) References Cited

U.S. PATENT DOCUMENTS 6,473,168 B1   10/2002   Ruymen
6,633,338 B1 * 10/2003   Pelsue ............... G01N 21/8806
                                            348/31

OTHER PUBLICATIONS

Written Opinion (PCT/ISA/237) issued on Jan. 14, 2015, by the European Patent Office as the International Searching Authority for International Application No. PCT/EP2014/073578.

* cited by examiner

INSPECTION APPARATUS

The present invention relates to an apparatus for inspecting a stream of matter, as well as a system comprising such an apparatus.

EP 1 185 854 discloses a detection station including a vertically downwardly directed video camera and a detection unit, which station has a stream of waste matter advanced therethrough on a substantially horizontal conveyor belt to a transverse array of air jet nozzles. The rectangular picture area of the camera spans the whole width of the belt and thus of the stream of waste. The data from the camera is used to identify the positions of individual objects in the waste stream (in the sense of approximately the region that the object occupies in the stream of waste). The unit scans the stream of waste along a rectilinear path P also extending the whole width of the belt and thus of the waste stream, the path P being perpendicular to the longitudinal direction D of the belt, i.e. to the feed direction of the waste stream. By infrared spectrum analysis, the unit detects the composition of at least some of the objects in the waste stream. The data from the camera and the unit are used to control a controller for solenoid valves which control the supply of compressed air to the respective nozzles. In this system, the composition and/or colour of each object is/are detected by the unit, whilst the video camera is used to monitor the scanned region and its data output employed automatically to detect the positions of the objects and to correct the data relating to those objects as received from detectors in the unit.

One issue related to the above system is that e.g. small objects may change position on the conveyor belt between being measured by the detection unit and the camera. Thus it might be difficult to determine which readings belong to which item.

It is an object of the present invention to provide an improved apparatus for inspecting a stream of matter. The present invention is defined in the independent claims, and embodiments are set forth in the appended dependent claims.

According to one aspect of the present invention, there is provided an apparatus for inspecting a stream of matter, which comprises a first and a second light source, a first and a second detector as well as a first scanning element and a first beam splitter. Said first light source is adapted to emit a first light beam comprising wavelengths within a first wavelength range ($\lambda_{1a}$-$\lambda_{1b}$), for illuminating said stream of matter from side to side; and the first detector is arranged to receive said first light beam after it has been reflected against said stream of matter at a first detection area.

The second light source is adapted to emit a second light beam comprising wavelengths within a second wavelength range ($\lambda_{2a}$-$\lambda_{2b}$), for illuminating said stream of matter at an illuminated area, wherein any wavelength ($\lambda_1$) in said first wavelength range is different from any wavelength ($\lambda_2$) in said second wavelength range (either $\lambda_{1b} < \lambda_{2a}$ or $\lambda_{2b} < \lambda_{1a}$). The second detector is arranged to receive said second light beam after it has been reflected against said stream of matter at a second detection area.

Moreover, the first scanning element is arranged between said stream of matter and said second detector and is adapted to redirect said second detection area from side to side across said stream of matter. Finally, the beam splitting element is arranged to receive said first light beam, after said first light beam has been reflected against said matter along a first optical axis; and is arranged to receive said second light beam, after said second light beam has been reflected against said matter also along said first optical axis. Said beam splitting element is further adapted to guide said reflected first light beam towards said first detector and to guide said reflected second light beam towards said second detector, by redirecting at least one of said reflected first light beam and said second reflected light beam along a second optical axis being non-parallel said first optical axis. More specifically said scanning element is arranged between said beam splitting element and said second detector to receive only said reflected second light beam of said reflected first and second light beams.

In relation to this invention the stream of matter which is inspected by the apparatus may be consist of any objects which is suitable for optic inspection, such as, but not limited to, ores and minerals, food and corps as well as collected waste and scrap.

According to one example said first light source may be selected from a group comprising lasers, supercontinuum lasers, halogen lamps, light emitting diodes, fluorescent tubes and combinations thereof.

According to one example said second light source may be selected from a group comprising halogen lamps, light emitting diodes, lasers and supercontinuum lasers and combinations thereof.

According to one example said beam splitting element is a dichroic beamsplitter such as but not limited to a dichroic mirror, a dichroic reflector, or a cube beam splitter.

Said first and second light sources are selected based on the optical properties of the objects in said stream of matter, and in more detail based on which optical properties of the objects in the stream of matter that are of interest.

According to one example, both said first light source and said second light source are line illuminations, that simultaneously illuminates the stream of matter from side to side. Examples of such illuminations are halogen lamps, LED-panels, or laser(s) provided with suitable optics.

According to another example, both said first light source and said second light source are spot illuminations, sweepingly illuminating said stream of matter from side to side. Examples of such illuminations are LEDs or laser(s) provided with suitable optics. Herein, the terms spot illumination and point illumination are used interchangeably.

According to yet another example, one of said first and second light sources is a line illumination, and the other of said first and second light sources is a point illumination.

According to a first specific example, said line illumination is a LED-panel comprising e.g. three rows of LEDs. The two outer rows consist e.g. of green LEDs arranged side by side. The middle row consists e.g. of groups of two IR, and one red LED, and between each group there is a gap. Furthermore, between each pair of red LEDs there are two IR LEDs. Each led is provided with optics which focuses the light on the stream of matter.

According to a second specific example, said point illumination is a combination of lasers having different wavelengths, such as red, green and IR, wherein the beams from the lasers are combined by polarizing beam splitters, so as to align the polarization of the laser beams, before the laser beams illuminates the stream of matter. In more detail, the first and the second laser beam (e.g. red and green) are combined by a first polarizing beam splitter to a intermediate beam (red/green), and the intermediate beam (red/green) is combined with the third laser beam (IR) by a second polarizing beam splitter into a resulting beam (red/green/IR). The lasers may e.g. be lit simultaneously, or one by one, or in pairs Moreover, according to one example said first light source is arranged according to said first specific example and said second light source is arranged according to said second specific example.

In relation to this invention the term wavelength range of a light source can be either a single wavelength, as 632.8 nm from a HeNe-laser; or a first wavelength band, as between 380-405 nm from a InGaN blue LED; or a wider wavelength band, as between about 450-650 nm from a white-light LED where GaN or InGaN blue source pumps Ce:YAG phosphor; or an even wider wavelength band, as between about 500-1500 nm from a Tungsten-Halogen lamp at 3 300 K.

In relation to this invention for a first light source adapted to emit a total spectrum ranging from e.g. 500-1500 nm, the first wavelength range of the first light source corresponds to the portion of this total spectrum that is received by the first detector e.g. 500-900 nm. In analogy, for a second light source adapted to emit a total spectrum ranging from e.g. 500-1500 nm, the second wavelength range of the second light source corresponds to the portion of this total spectrum that is received by the second detector e.g. 1100-1500 nm.

In relation to this invention, the expression that any wavelength ($\lambda_1$) in a first wavelength range is different from any wavelength ($\lambda_2$) in a second wavelength range means either that all wavelength in said first wavelength range is shorter than any wavelength ($\lambda_2$) in a second wavelength range or that all wavelength in said first wavelength range is longer than any wavelength ($\lambda_2$) in a second wavelength range.

In relation to this invention a stream of matter is illuminated by at least a first and a second light source. The stream of matter has a net direction of motion, and the width of the stream is measured in a direction orthogonal to said net direction of motion. These first and second light sources may each illuminate the whole width of the stream, or may illuminate a portion there of. In order to get a higher resolution, two apparatus may be used side by side; each one having a first and a second light source, which are arranged such that the area illuminated by the respective apparatus is partly overlapping, such that the whole width of the stream is illuminated only when both apparatuses are used. The light sources are all arranged to illuminate the same side, or the same face, of the stream. According to another example three or more apparatuses are arranged side by side, such that the whole stream is illuminated by overlapping light sources of the different apparatuses. According to another example, only a portion of the stream is inspected, e.g. as sampling is sufficient. In this case one apparatus may be used which light sources only illuminate a portion e.g. between 20% and 80% of the width of the stream.

In other words, in all cases there is a stream of matter comprising objects that are inspected and this inspected stream is illuminated from side to side, i.e. from one side of the stream to the other, across the stream. The inspected stream may correspond to the total stream of matter or a portion thereof, and hence the total stream or a portion thereof is illuminated from side to side by said apparatus.

That the stream of matter is illuminate from side to side includes that the stream of matter is illuminated transversely of its feed direction. Moreover, the light sources can be arranged such that the area illuminated by the light sources is orthogonal to the net direction of motion of the stream of matter (called orthogonal illumination), or can be arranged such that the area illuminated by the light sources is offset by +/−45° from the orthogonal illumination.

The illumination from a light source can be simultaneous or sweeping, i.e. the portion of the stream inspected by a respective apparatus (below called "the inspected stream") may be illuminated simultaneously from side to side across the stream, i.e. the whole width of the inspected stream is illuminated at once; or may be illuminated sweepingly from side to side across the stream, i.e. the illuminated portion of the inspected stream (also called illuminated area) is moved from one side of the inspected stream to the other by means of a redirecting element, such as a moving mirror or the like. The illuminated area may have any shape, such as (but not limited to) a point, a spot, a circle, a line, a rectangle, a square or a combination of these. In other words, when the inspected stream is sweepingly illuminated from side to side, only a portion of the width of the stream is illuminated at each instance in time; and when the inspected stream is simultaneously illuminated from side to side, the whole width of the inspected stream is illuminated at least one instance in time.

According to one example, there is provided a system comprising a first and a second apparatus, each arranged as described above, wherein said first apparatus is adapted to inspect a first portion of said stream, and said second apparatus is adapted to inspect a second portion of said stream, said first and second portions being only partly overlapping. Said first and second apparatus may be arranged side by side.

According to one example, said apparatus comprises a first redirecting element arranged to receive said second light beam from said second light source and being adapted to redirect said second light beam so as to sweepingly illuminate said stream of matter from side to side.

According to yet one example, said scanning element and said first redirecting element is one and the same.

According to yet one example, said apparatus further comprises a second scanning element arranged between said stream of matter and said first detector, said second scanning element being adapted to redirect said first detection area from side to side across said stream of matter.

According to yet one example, said apparatus further comprises a second redirecting element, arranged between said first light source and said stream of matter, and being adapted to receive said first light beam from said first light source and to redirect said first light beam so as to sweepingly illuminate said stream from side to side.

In relation to this invention the term cutting wavelength, or cutting wavelength of the beam splitting element, is used to describe at which wavelength the division in a shorter wavelength range and longer wavelength range is made.

In other words, the beam splitting element will divide the light reflected from said stream of matter into two portions. One portion comprising wavelengths lower than the cutting wavelength, and another portion comprising wavelengths longer than and equal to the cutting wavelength. One of these portions is thereafter forwarded to the first detector and the other is forwarded to the second detector.

In other words, said first scanning element may be arranged, between said beam splitting element and said second detector, in any of the two portions of light reflected from said stream of matter. I.e. it may be arranged in the portion comprising wavelengths shorter than the cutting wavelength or in the portion comprising wavelengths longer than the cutting. Hence, of said first and second reflected light beams, the first scanning element receives only said second reflected light beam.

In practice, in said portion comprising wavelength which are shorter than the cutting wavelength, there are normally also wavelength which are longer than said cutting wavelength; and in said portion comprising wavelength which are longer than the cutting wavelength there are normally also wavelengths which are shorter than said cutting wavelength, due to e.g. the characteristics of the the beam splitting element.

However, when looking at the energy content of the said portion comprising wavelength which are shorter than the cutting wavelength, a major part of the energy content is constituted by wavelengths being shorter than the cutting wavelength, and a minor part of the energy content is constituted by wavelengths being longer than the cutting wavelength. The energy content is computed using the formula $E=hc/\lambda$, where E is the energy of a photon, h is Planck's constant and c is the speed of light. According to one example more than 80%, or more than 90%, or more than 95%, of the energy content is constituted by wavelengths being shorter than the cutting wavelength.

Furthermore, when looking at the energy content of said portion comprising wavelength which are longer than the cutting wavelength, a major part of the energy content is constituted by wavelengths being longer than the cutting wavelength, and a minor part of the energy content is constituted by wavelengths being shorter than the cutting wavelength. According to one example more than 80%, or more than 90%, or more than 95%, of the energy content is constituted by wavelengths being longer than the cutting wavelength. According to one example, said beam splitting element is adapted to guide said reflected second light beam towards said second detector along a second optical axis and to guide said reflected first light beam towards said first detector along a third optical axis, and wherein the angle between said second optical axis and said third optical axis is between 20° to 160°, or between 60° to 120°, or between 80° to 100°.

The first light source may be adapted to emit a first spectrum, e.g. 632.8 nm or 450-650 nm, and the second light source may be adapted to emit a second spectrum, e.g. 500-1500 nm, which spectrums are partly overlapping. When the spectrums are partly overlapping it may be advantageous to arrange a filtering element between one of the light sources and said matter to be sorted, which filtering element is adapted to transmit or forward only wavelengths within the wavelength range of that light source. In other words, when a filtering element is arranged between the first light source and the matter to be sorted, it preferably transmits or forwards wavelengths within said first wavelength range. Alternatively, or additionally, when the filtering element arranged between said second light source and said stream of matter, it is adapted to block wavelength within said first wavelength range. Alternatively, or additionally when a filtering element is arranged between said first light source and said stream of matter, it is adapted to block wavelength within said second wavelength range.

According to one example, said first detector comprises a CCD, and additionally or alternatively said first detector is a line detector or an area detector. Fixed or adjustable filters, for filtering out a desired wavelength range, may be provided in front of said first detector. If adjustable filters are used, different wavelength ranges may be filtered out consecutively. Additionally or alternatively, different filters may be provided in front of different parts of the detector, such that different areas of the detector receive different wavelengths.

According to one example, said second detector comprises a CCD, additionally or alternatively said second detector is a line detector or an area detector. Additionally or alternatively, said second detector may be a spectrometer or a sensor of a hyperspectral system. Fixed or adjustable filters, for filtering out a desired wavelength range, may be provided in front of said second detector. If adjustable filters are used, different wavelength ranges may be filtered out consecutively. Additionally or alternatively, different filters may be provided in front of different parts of the detector, such that different areas of the detector are sensitive to different wavelengths.

In relation to this invention the term first detection area refers a portion of the stream of matter that is viewed by said first detector at one instance in time; and the term second detection area refers a portion of the stream of matter that simultaneously is viewed by said second detector at one instance in time. A detection area may cover the whole width of the inspected stream, or may cover only a portion thereof. When said detection area covers only a portion of the inspected stream, the detection area is moved or swept from side to side of the inspected stream by means of a redirecting element, such as a moving mirror or the like. The moving mirror is e.g. a polygon mirror or a tilting mirror.

According to one example, both said first and second light sources simultaneously illuminate the inspected stream from side to side across the stream, or the whole width of the inspected stream, the first detection area simultaneously covers the inspected stream from side to side, whereas the second detection area only coverers a portion of the whole width of the inspected stream and thus sweepingly covers the inspected stream from side to side.

According to another example, said first light source simultaneously illuminate the inspected stream from side to side, the second light source sweepingly illuminates the inspected stream from side to side, the first detection area simultaneously covers the inspected stream from side to side, whereas the second detection area only coverers a small portion of the inspected stream and sweepingly covers the inspected stream from side to side. Here, either two different redirecting elements may be used, one which redirects the illuminated area and one which redirects the detection area. Alternatively, the same redirecting element is used for redirecting both the illuminated area and the detection area.

According to one example the illumination from a lit light source is one and the same over time, which includes natural variations due to aging, variations in the power supply etc. According to another example the illumination from a light source varies over time according to a predetermined pattern, e.g. there may be a variation in colour or intensity distribution. E.g. three colours may be cycled. The variation in colour may be achieved by use of different light sources, or by use of a rotating filter in front of a light source having a wide spectrum.

Furthermore, said light sources may be pulsed or continuous.

The stream of matter may be transported by any means, such as but not limited to being in free fall path, being transported in a chute or on a conveyor belt.

According to one example, there is provided a system comprising an apparatus arranged as described above, and transportation means for transporting the stream of matter, said transportation means preferably including at least one of a conveyor belt, a chute and a free fall path.

According to one example, there is provided a system comprising a first and a second apparatus, each arranged as described above, wherein said first apparatus is adapted to inspect a first face of said stream, and said second apparatus is adapted to inspect a second face of said stream, said first and second faces being opposite faces of said stream. In other words, the stream of matter is arranged to pass between said first and second apparatuses, e.g. in free fall or on a transparent conveyour. The apparatuses may be arranged to inspect substantially the same part of the stream, however from two opposing sides. These parts may be separated from each other, overlapping or coinciding. In other words, the area inspected by said first and second apparatus may be adjacent to each other.

The apparatus may be an inspecting apparatus, measuring different properties of the objects passing in the stream. It may also be a sorting apparatus which, based on the measured properties, makes a decision whether a specific object in the stream of matter is to be kept or sorted out.

According to one example, there is provided a system comprising one or more apparatus(es) arranged as described above. Further, the stream of matter to be inspected comprises objects, and said system further comprises processing means adapted to receive detection-data from said first detector and said second detector, and to transform said detection-data into sorting-data; and removing means that is adapted to receive the sorting-data from said processing means and to remove objects from said stream of matter in dependence on said sorting-data. The objects that are removed could be directed to one common, or if desired to several different spots dependent on the detection data. Examples of removing means, or means for sorting out objects, are nozzles and ejectors.

Details about how detection-data may be processed to determine if an object should be removed or not, how detection-data may be processed to result in sorting-data as well as how removing means may be formed and controlled are well known in the art and therefore not described further in this application.

The present invention will now be described in more detail, with reference to the appended drawings showing embodiments of the invention.

FIG. 1a is a schematic perspective view of an apparatus according to the invention, wherein said first and second light sources are line illuminations.

FIG. 1b is a schematic top view illustrating the illuminated areas and field of views of the apparatus described in relation to FIG. 1a.

FIG. 2a is a schematic perspective view of an apparatus according to the invention, wherein said first light source is line illumination, and said second light source is swept by means of a polygon mirror.

FIG. 2b is a schematic top view illustrating the illuminated areas and field of views of the apparatus described in relation to FIG. 2a.

Figures 1A, 1B:
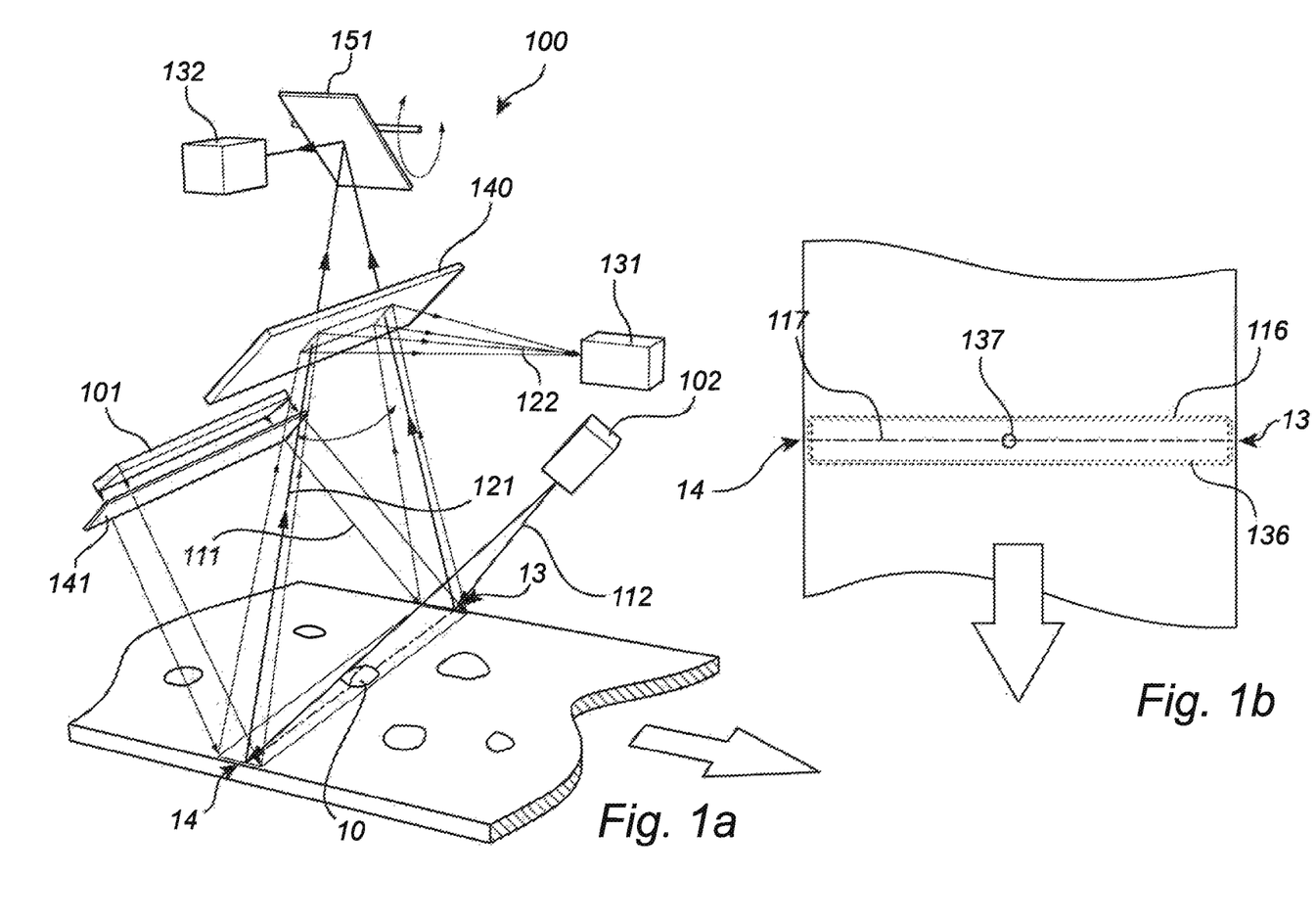

FIG. 1 schematically illustrates an apparatus 100 for inspecting a stream of matter 10. The arrows in FIG. 1a and 1b illustrate the transport direction of the stream of matter, or the net direction of motion of said matter, or the feed direction.

The apparatus 100 comprises a first light source 101, which is adapted to emit a first light beam 111 comprising wavelengths within a first wavelength range ($\lambda_{1a}$-$\lambda_{1b}$) for illuminating said stream of matter from side to side. The first light source is a line illumination which simultaneously illuminates said stream of matter 10 from one side 13 to the other 14.

The apparatus 100 also comprises a second light source 102 adapted to emit a second light beam 112 comprising wavelengths within a second wavelength range ($\lambda_{2a}$-$\lambda_{2b}$), for illuminating said stream of matter at a second illuminated area 117. The second light source is a line illumination which simultaneously illuminates said stream of matter 10 from one side 13 to the other 14. Further any wavelength ($\lambda_1$) in said first wavelength range of said first light source is different from any wavelength ($\lambda_2$) in said second wavelength range of said second light source ($\lambda_{1b} < \lambda_{2a}$ or $\lambda_{2b} < \lambda_{1a}$).

The first light beam 111 is reflected by said stream of matter towards a beam splitting element 140. The beam splitting element 140 is arranged to receive said first light beam 111, after it has been reflected against said matter along a first optical axis 121; and arranged to receive said second light beam 112, after said second light beam has been reflected against said matter also along said first optical axis 121 The beam splitting element 140, e.g. a dichroic mirror, is further adapted to guide said reflected first light beam 111 towards a first detector 131; and to guide said reflected second light beam 112 towards said second detector 132 by redirecting one of said reflected first light beam and said reflected second light beam along a second optical axis 122 non-parallel said first optical axis 121. More specifically said scanning element 151 is arranged between said beam splitting element 140 and said second detector 132 to receive only said reflected second light beam of said reflected first and second light beams.

Moreover, said first detector 131 is adapted to receive said first light beam 111 after it has been reflected against said stream of matter 10 at a first detection area 136; and said second detector 132 is adapted to receive said second light beam 112 after it has been reflected against said stream of matter 10 at a second detection area 137. Furthermore, a first scanning element 151 is arranged between said stream of matter 10 and said second detector 132 and being adapted to redirect said second detection area 137 from side to side across said stream of matter.

FIG. 1b illustrates the first illuminated area 116, or the area 116 illuminated by said first light source 101. According to this example the first light source is a line illumination comprising LED-lamps which simultaneously illuminates the whole width of the stream, and the first illuminated area is a rectangle extending from side to side across the stream of matter. The LED-lamps may be pulsed or continuous. Further, according to this example the first detector 131 is a line detector or area detector (the sensors in the detector are arranged in a line or a matrix) adapted to simultaneously detect the whole width of the stream of matter. The field of view 136 of said first detector or the first detection area 136 corresponds to a rectangle extending from side to side across the stream of matter. The first detection area 136 is within said first illuminated area 116.

Furthermore, the area 117 illuminated by said second light source 102, or the second illuminated area 117 is also indicated in FIG. 1b. According to this example the second light source is a line illumination comprising a laser, and the second illuminated area is line extending from side to side across the stream of matter. The laser may be pulsed or continuous. Further, according to this example the second detector 132 is spectrometer adapted to sweepingly detect the whole width of the stream of matter. The field of view 137 of said second detector or the second detection area 137 corresponds to a spot. The field of view 137 of said second detector or the second detection area 137 is moved from side to side across the stream of matter by means of a scanning element 151, here a tilting mirror.

According to a first example said first and second light sources are adapted to illuminate the stream of matter both at the same time. According to a second example said first and second light sources are adapted to illuminate the stream of matter consecutively, i.e. first said first light source is lit and thereafter said second light source is lit, and thereafter the lighting sequence is repeated over and over again. According to a third example, a combination of examples one and two is used, i.e. the light sources are sometimes lit simultaneously, and sometimes lit consecutively according to a predetermined illumination sequence.

The first light source may be any suitable illumination and comprise e.g. a laser, light emitting diodes, fluorescent tubes or combination of these. The first light source may emit radiation in the ultra violet range (UV) visible range (VIS), near infrared range (NIR), or mid infrared range (MIR) or in a combination of these ranges.

The second light source may be any suitable illumination and comprise e.g. halogen lamps. The second light source may emit radiation in the ultra violet range (UV), visible range (VIS), near infrared range (NIR), or mid infrared range (MIR) or in a combination of these ranges.

Optionally, a filter element may be arranged between the first light source and the stream of matter, which filter element is e.g. selected such that it removes wavelengths emitted by said first light source which disturbs the second detector; additionally or alternatively a filter element may be arranged between the first light source and the stream of matter, which filter element is e.g. selected such that it removes wavelengths emitted by said first light source which disturbs the second detector.

According to one example, the wavelengths of said first wavelength range is shorter than the wavelengths of said second wavelength range. Further, said second light source emits wavelengths not only in said second wavelength range but also within the interval of said first wavelength range and the cutting wavelength of said beam splitter, which wavelengths are disturbing to the measurements performed by using said first detector. A filter element may arranged between said second light source and said stream of matter, which filter element removes the wavelengths emitted by said second light source which is shorter than said cutting wavelength, or said filter element removes the wavelengths which are within the interval of said first wavelength range and the cutting wavelength of said beam splitter. Hence, the second light source does not disturb the first detector.

According to one example, the wavelengths of said first wavelength range is shorter than the wavelengths of said second wavelength range. Further, said first light source emits wavelengths not only in said first wavelength range but also within the interval of said second wavelength range and the cutting wavelength of said beam splitter, which wavelengths are disturbing to the measurements performed by using said second detector. A filter element may be arranged between said first light source and said stream of matter, which filter element removes the wavelengths emitted by said first light source which is longer than or equal to said cutting wavelength, or said filter element removes the wavelengths which are within the interval of said second wavelength range and the cutting wavelength of said beam splitter. Hence, the first light source does not disturb the second detector.

Analogous solutions may be applied when the wavelengths of said first wavelength range is longer than the wavelengths of said second wavelength range.

Figures 2A, 2B:
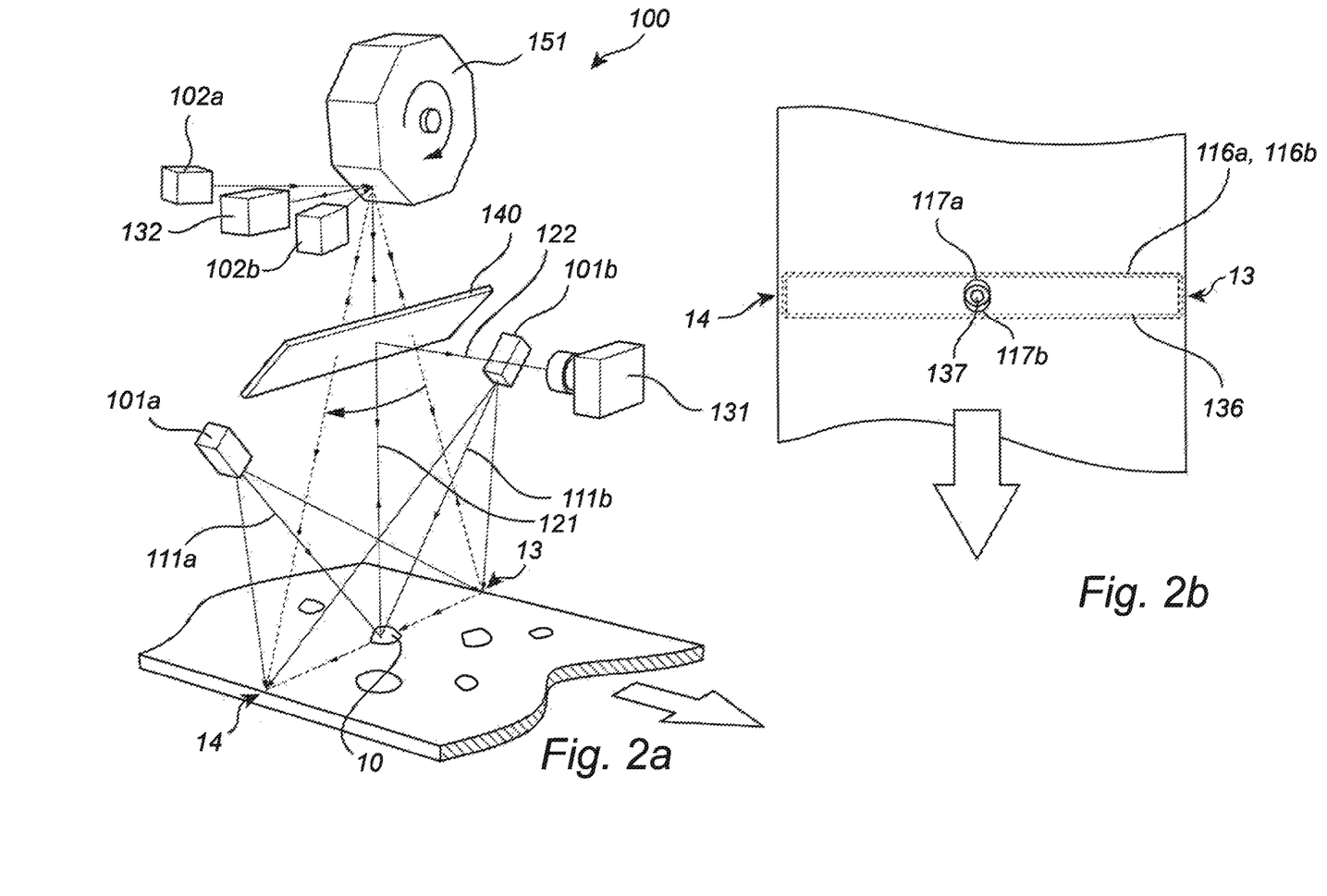

The apparatus illustrated in FIGS. 2a and 2b is equal to the one described in relation to FIGS. 1a and 1b, except for the details mentioned below. The tilting mirror is replaced by a polygon mirror 151, which is arranged to rotate around its central axis, e.g. by means of a motor (not shown). The second illumination is not a line illumination but a spot illumination. The first light source 101 comprises two separate lamps 101a, 101b, arranged one on each side of the stream of matter. Both lamps illuminates substantially the same first illuminated area 116 on the stream of matter. The second light source 102 comprises two separate light sources 102a, 102b. The area 117a, 117b illuminated by said second light source 102, or the second illuminated area 117a, 117b is indicated in FIG. 1b. According to this example the second light source is a point illumination comprising a laser, illuminating only a portion of said stream of matter. The laser may be pulsed or continuous. The redirecting element 151 is arranged to sweepingly move the second illuminated area 117a, 117b from side to side across said stream of matter.

Further, according to this example the second detector 132 is spectrometer adapted to sweepingly detect the whole width of the stream of matter. The field of view 137 of said second detector or the second detection area 137 corresponds to a spot. The field of view 137 of said second detector or the second detection area 137 may be moved from side to side across the stream of matter by means of a scanning element 151, here a polygon mirror. The second detection area 137 is within the area illuminated by said second light source 117a, 117b.

In other words, said second light source 102 illuminates said stream of matter 10 at a second illuminated area 117a, 117b covering only a portion of the width of said stream of matter, and a redirecting element 151 is arranged to receive said second light beam 112a, 112b from said second light source 102 and is adapted to redirect said second light beam so as to move said first illuminated area 117a, 117b from side to side across said stream of matter, wherein preferably said redirecting element and said first scanning element, described in relation to FIG. 1a, is one an the same.

Figure 5:
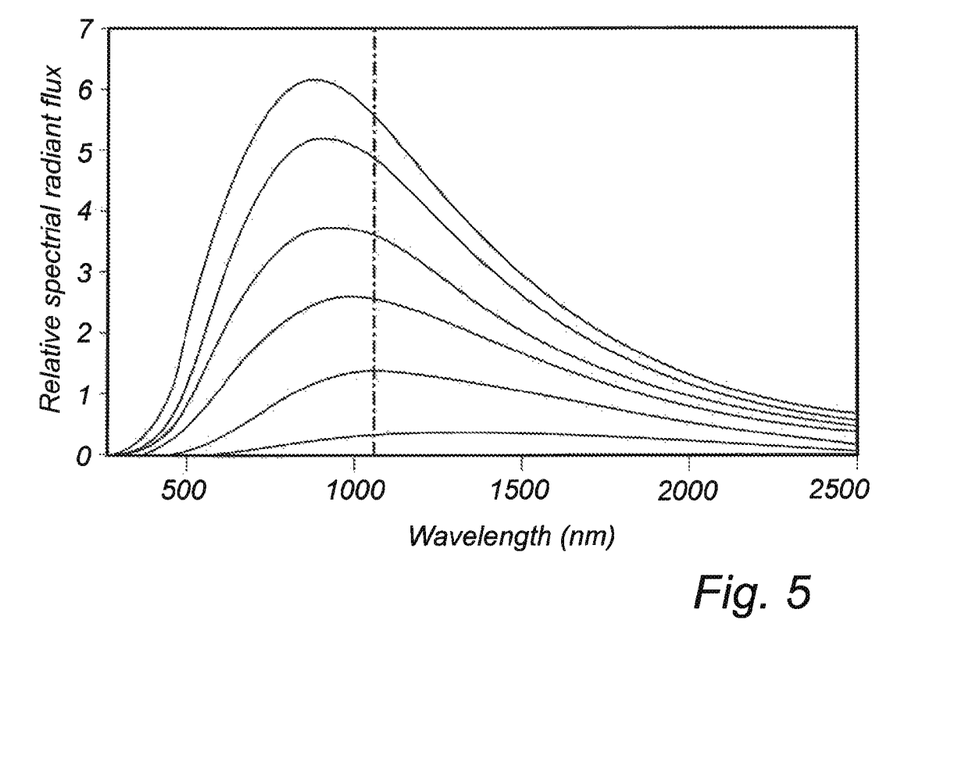
FIG. 5 exemplifies the spectrum of different halogen lamps.
Figure 6:
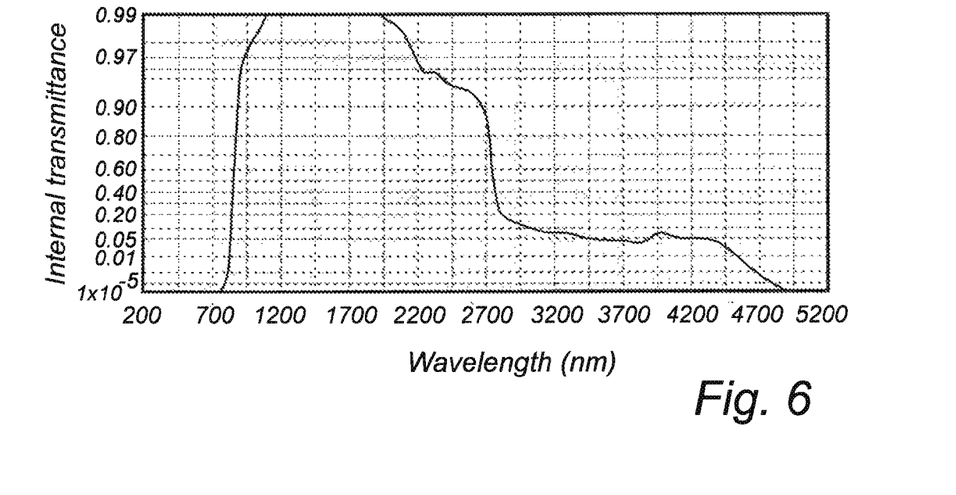
FIG. 6 exemplifies the transmittance of a filter.
Figure 7:
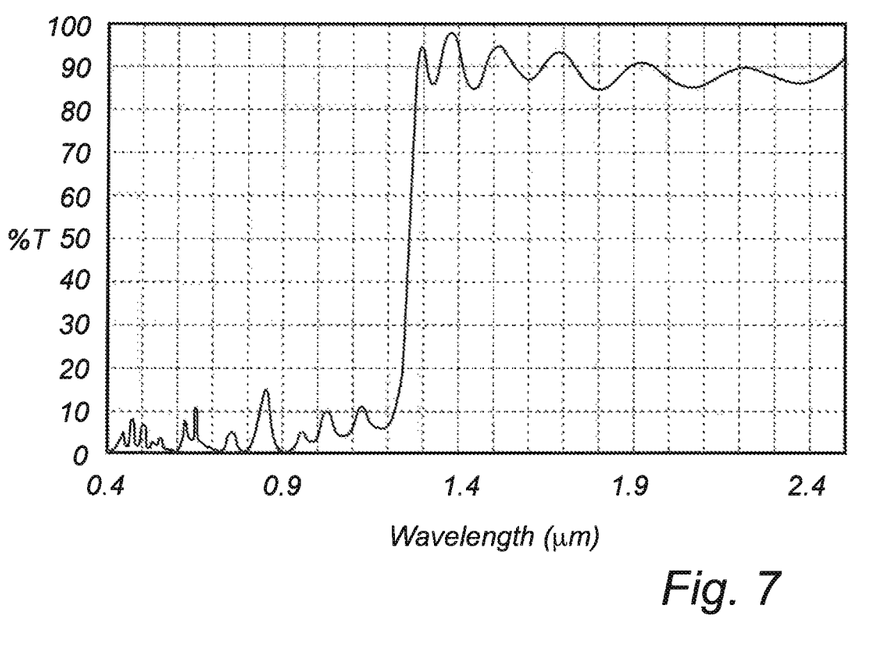
FIG. 7 exemplifies the transmittance of a beam splitter.

According to one detailed example the first light source comprises LEDs emitting white light, e.g. Z-Power LEDs being manufactured by Seol Semiconductor and emitting Pure White light; and in more detail belonging to e.g. the A0-A5, B0-B5 or C0-C5 binning described in more detail in the product specification, i.e. roughly within the CIE coordinates (0.3028, 0.3304) (0.3552, 0.3760) (0.3514, 0.3487) (0.3068, 0.3113) (0.3028, 0.3304). The LEDs simultaneously illuminates the stream of matter from side to side. The second light source is one of the halogen lamps, which spectrums are illustrated in FIG. 5. The top line is the spectral distribution of a lamp of 3 300 K, the one below is the spectral distribution of a lamp of 3 200 K, the one below that is the spectral distribution of a lamp of 3 000 K, the one below that is the spectral distribution of a lamp of 2 800 K, the one below that is the spectral distribution of a lamp of 2 500 K and the bottom one is the spectral distribution of a lamp of 2 000 K. The second light source simultaneously illuminates the stream of matter from side to side. A filter having the transmittance illustrated in FIG. 6, i.e. a cut on wavelength at about 850 nm, is arranged between the second light source and the stream of matter. A dichroic mirror having a transmittance as illustrated in FIG. 6, i.e. a cutting wavelength at about 1 200 nm, is selected as beam splitting element. The first detector is an RGB-camera and the second detector is a NIR spectrometer. The cutting wavelength (about 1 200 nm) of the spectrometer is also indicated in FIG. 5.

When the first and second light sources are lit simultaneously, light from both light sources reaches the beam splitter and is divided into a first portion substantially consisting of wavelength lower than said cutting wavelength, and a second portion substantially consisting of wavelength longer than said cutting wavelength. The first portion is reflected by said beam splitter towards the first detector, and the second portion is transmitted by said beam splitter towards said second detector. In other words, substantially only light from said first light source is transmitted to said first detector, and substantially only light from said second light source is transmitted to said second detector.

In practice, in said first portion there are wavelength which are longer than said cutting wavelength, and in said second portion there are wavelengths wavelength which are shorter than said cutting wavelength, due to the characteristics of the filter and the beam splitter.

However, when looking at the energy content of the first portion, a major part of the energy content is constituted by wavelengths being shorter than the cutting wavelength, and a minor part of the energy content is constituted by wavelengths being longer than the cutting wavelength. The energy content is computed using the formula $E=hc/\lambda$, where E is the energy of a photon, h is Planck's constant and c is the speed of light. In more detail, more than 80%, or more than 90%, or more than 95%, of the energy content is constituted by wavelengths being shoter than the cutting wavelength.

Furthermore, when looking at the energy content of the second portion, a major part of the energy content is constituted by wavelengths being longer than the cutting wavelength, and a minor part of the energy content is constituted by wavelengths being shorter than the cutting wavelength. In more detail, more than 80%, or more than 90%, or more than 95%, of the energy content is constituted by wavelengths being longer than the cutting wavelength.

An illumination of said stream of matter from side to side includes, but is not limited to, an illumination which is orthogonal to the transport direction of said stream of matter. As indicated in FIG. 3, an illumination of said stream of matter from side to side may be off-set from an orthogonal illumination by e.g. 25°.

Figure 4:
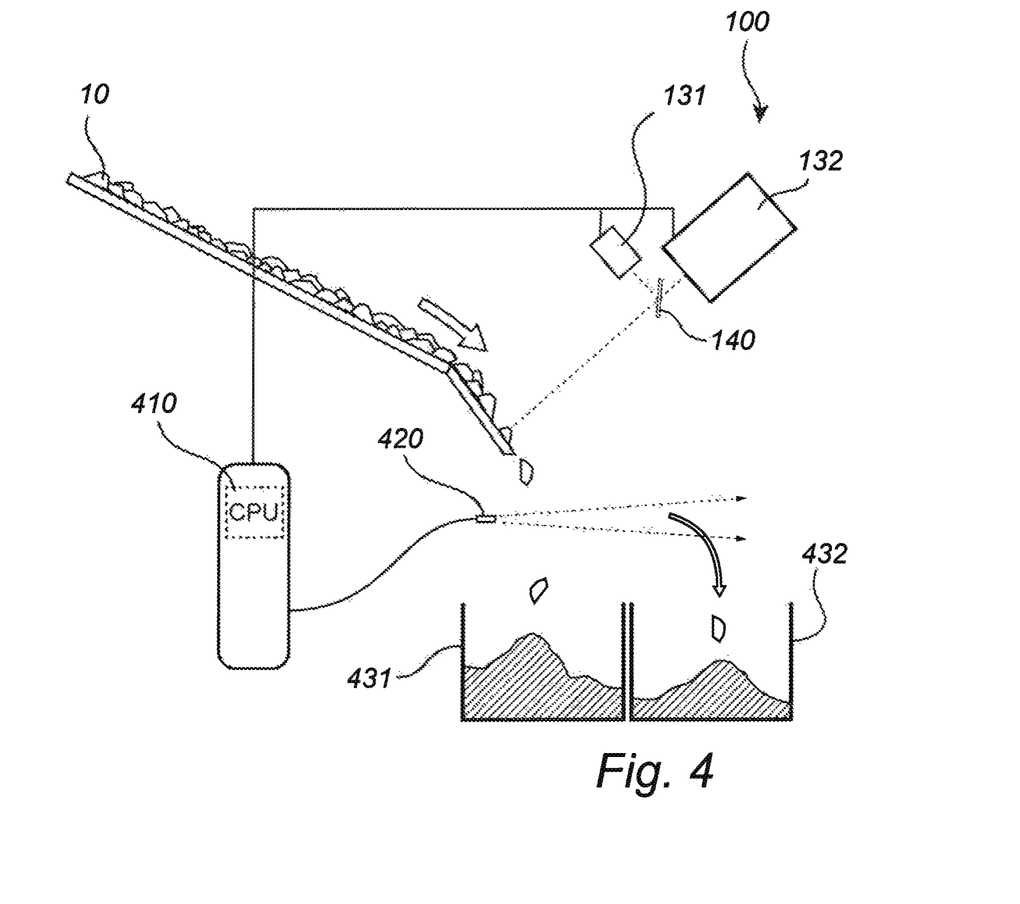
FIG. 4 schematically illustrates the use of the apparatus for a sorting a stream of matter on a conveyor belt.

FIG. 4 illustrates one application of the apparatus described above. Light reflected from a stream of matter is received by a beam splitting element 140, and split into two portions dependent on wavelength, and each portion is forwarded to a respective detector 131, 132. Based on properties determined by the respective detector and analyzed by a processing apparatus 410; the objects 10 in the stream of matter are sorted into a first or a second container 431, 432 by use of a sorting apparatus 420 utilizing presurized air. I.e. when an object is to be put in the right container a puff of air is emitted which pushes the object into the right container.

Figure 3:
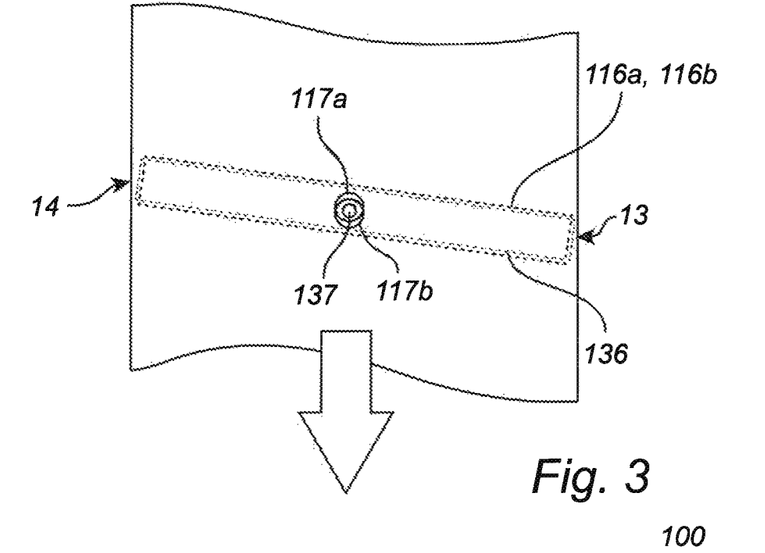
FIG. 3 illustrates an alternative orientation of the illuminated areas and field of views.

In other word, there is provided a system comprising an apparatus arranged as described e.g. in relation to FIGS. 1-3. Further, the stream of matter to be inspected comprises objects 10, and said system further comprises processing means 410 adapted to receive detection-data from said first detector and said second detector 131;132 and to transform this into sorting data; and removing means 420 adapted to receive sorting-data from said processing means and to remove objects from said stream of matter in dependence on said sorting-data. The sorting data may e.g. be indicative of whether the objects are to be put in the left or right container 431, 432. Furthermore, the objects that are removed could be directed to one common, or alternatively to several different spots dependent on the detection data.

The person skilled in the art will realize that the present invention by no means is limited to the embodiment(s) described above. On the contrary, many modifications and variations are possible within the scope of the appended claims.

For example, the illumination may be arranged beneath the stream of matter instead of above it, provided the coveyour is transparent. The conveyour may be replaced by a chute or a free fall path. The scanning element may be arranged between said beam splitter and said second detector, in a light path that is redirected by said beam splitting element, i.e. in a light path that is non-parallel with said first optical axis. Moreover, additional light sources and detectors may be used, having a similar set up to what has been described above, i.e. where the light passes the dichroic mirror before reaching the detector. Furthermore, the combinations of light sources and detectors can be chosen freely, as long as the principles described herein are employed.

The invention claimed is:

1. An apparatus for inspecting a stream of matter, the apparatus comprising:
    a first light source being adapted to emit a first light beam comprising wavelengths within a first wavelength range $(\lambda_{1a}-\lambda_{1b})$ for illuminating said stream of matter from side to side and,
    a first detector arranged to receive said first light beam after it has been reflected against said stream of matter at a first detection area,
    a second light source adapted to emit a second light beam comprising wavelengths within a second wavelength range $(\lambda_{2a}-\lambda_{2b})$ for illuminating said stream of matter at an illuminated area, wherein any wavelength $(\lambda_1)$ in said first wavelength range is different from any wavelength $(\lambda_2)$ in said second wavelength range
    a second detector being arranged to receive said second light beam after it has been reflected against said stream of matter at a second detection area,
    a first scanning element being arranged between said stream of matter and said second detector and being adapted to redirect said second detection area from side to side across said stream of matter,
    further comprising
    a beam splitting element arranged to receive said first light beam, after said first light beam has been reflected against said matter along a first optical axis, and arranged to receive said second light beam, after said second light beam has been reflected against said matter also along said first optical axis,
    wherein said beam splitting element is adapted to guide said reflected first light beam towards said first detector and to guide said reflected second light beam towards said second detector by redirecting one of said reflected first light beam and said reflected second light beam along a second optical axis non-parallel said first optical axis and
    wherein said scanning element is arranged between said beam splitting element and said second detector to receive only said reflected second light beam of said reflected first and second light beams.

2. An apparatus according to claim 1, wherein said second light source is adapted to illuminate said stream of matter simultaneously from side to side.

3. An apparatus according to claim 1, further comprising a first redirecting element arranged to receive said second light beam from said second light source and being adapted to redirect said second light beam so as to sweepingly illuminate said stream from side to side.

4. An apparatus according to claim 3, wherein said redirecting element and said first scanning element is one and the same.

5. An apparatus according to claim 1, further comprising a second scanning element arranged between said stream of matter and said first detector, said second scanning element being adapted to redirect said first detection area from side to side across said stream of matter.

6. An apparatus according to claim 5, further comprising a second redirecting element adapted to receive said first light beam from said first light source and to redirect said first light beam so as to sweepingly illuminate said stream from side to side.

7. An apparatus according to claim 1, wherein said first light source is adapted to illuminate said stream of matter simultaneously from side to side.

8. An apparatus according to claim 1,
wherein said beam splitting element is adapted to guide said reflected second light beam towards said second detector along a second optical axis and to guide said reflected first light beam towards said first detector along a third optical axis, and wherein
the angle between said second optical axis and said third optical axis is between 20° to 160°, or between 60° to 120°, or between 80° to 100°.

9. An apparatus according to claim 1,
wherein said scanning element is one of a polygon mirror and a tilting mirror.

10. An apparatus according to claim 1,
wherein said first light source is selected from a group comprising lasers, supercontinuum lasers, halogen lamps, light emitting diodes, fluorescent tubes and combinations thereof.

11. An apparatus according to claim 1,
wherein said second light source is selected from a group comprising halogen lamps, light emitting diodes, lasers and supercontinuum lasers and combinations thereof.

12. An apparatus according to claim 1,
wherein the first light source is adapted to emit a first spectrum and said second light source is adapted to emit a second spectrum, wherein said first and second spectrums are partly overlapping.

13. An apparatus according to claim 12, wherein said apparatus further comprises a filtering element arranged between said second light source and said matter to be sorted, which filtering element is adapted to block wavelength within said first wavelength range ($\lambda_{1a}$-$\lambda_{1b}$).

14. An apparatus according to claim 1,
wherein said beam splitter is a dichroic mirror.

15. An apparatus according to claim 1,
wherein said first detector is one of a line detector and an area detector.

16. A system comprising a first and a second apparatus, each according to claim 1,
wherein said first apparatus is adapted to inspect a first portion of said stream, and said second apparatus is adapted to inspect a second portion of said stream, said first and second portions being only partly overlapping.

17. A system comprising an apparatus according to claim 1 and transportation means for transporting the stream of matter, said transportation means including at least one of a conveyor belt, a chute and a free fall path.

18. A system comprising a first and a second apparatus, each according to claim 1,
wherein said first apparatus is adapted to inspect a first face of said stream, and said second apparatus is adapted to inspect a second face of said stream, said first and second faces being opposite faces of said stream.

19. A system according to claim 18, wherein the area inspected by said first and second apparatus are adjacent to each other.

20. A system comprising an apparatus according to claim 1, wherein said stream of matter comprises objects, and said system further comprises
processing means adapted to receive detection-data from said first detector and said second detector and to transform said detection-data into sorting-data; and
removing means adapted to receive sorting-data from said processing means and to remove objects from said stream of matter in dependence on said sorting-data.

21. An apparatus according to claim 1, wherein said first wavelength range ($\lambda_{1a}$-$\lambda_{1b}$) is reflected by said beam splitting element, and said second wavelength range ($\lambda_{2a}$-$\lambda_{2b}$) is transmitted by said splitting element.

22. An apparatus according to claim 1, wherein the wavelengths in said first wavelength range is shorter than the wavelength in said second wave length range ($\lambda_{1b}<\lambda_{2a}$).

* * * * *